United States Patent [19]

Thomas

[11] Patent Number: 4,806,353

[45] Date of Patent: Feb. 21, 1989

[54] MOLD INHIBITING PRODUCT

[76] Inventor: Richard D. Thomas, 812 N. Euclid St., Fullerton, Calif. 92632

[21] Appl. No.: 606,150

[22] Filed: May 2, 1984

Related U.S. Application Data

[63] Continuation-in-part of Ser. No. 536,262, Sep. 27, 1983, abandoned.

[51] Int. Cl.$^4$ .................... A01N 37/00; A01N 59/20
[52] U.S. Cl. ............................. 424/141; 424/131; 424/144; 424/147; 424/150; 424/154; 514/557
[58] Field of Search ................ 424/317, 141, 131; 514/557

[56] References Cited

U.S. PATENT DOCUMENTS

| | | | |
|---|---|---|---|
| 2,217,905 | 10/1940 | Hoffman et al. | 424/317 |
| 3,404,987 | 10/1968 | Kooistra et al. | 424/317 |
| 4,042,716 | 8/1977 | Bertram et al. | 424/317 |

Primary Examiner—Leonard Schenkman
Attorney, Agent, or Firm—Albert L. Gabriel

[57] ABSTRACT

A mold inhibitor composition that has particular utility for the preservation of animal feeds, and a method of making such composition. The composition is an aqueous solution of one or more salts or propionic acid, one or more deliquescent materials, one or more humectants, and in certain forms of the invention monosodium glutamate is included. This composition makes propionate ions available for mold control just as effectively as propionic acid, but without either the bad odor or the serious corrosive characteristics of propionic acid. The deliquescent material serves the surprising function of keeping moisture from accumulating in feed adjacent the walls of feed bins or from condensing on the walls to minimize mold in this heretofore uncontrollable region. The method of the invention minimizes the normally severe precipitation problem that occurs when a base is mixed with propionic acid to form a propionate salt, by diluting out the number of molecules of the propionic acid and the base per unit of space as much as possible with the ingredients of the final product prior to the encounter between the propionic acid and the base.

20 Claims, No Drawings

MOLD INHIBITING PRODUCT

RELATED APPLICATION

The present application is a continuation-in-part, of Ser. No. 536,262, filed Sept. 27, 1983 abandoned for MOLD INHIBITING PRODUCT AND METHOD OF MAKING SAME.

BACKGROUND OF THE INVENTION

1. Field of the Invention

The present invention is in the field of mold inhibitors and methods for making same, and it relates particularly to mold inhibitors for animal grain feeds.

2. Description of the Prior Art

There is a serious worldwide problem of molds growing in food materials, and particularly in animal feeds. This problem is most serious, and is a year-round problem, in tropical zones of both the eastern and western hemispheres, but it is also a problem in temperate and colder zones, particularly during the spring and fall seasons when there are frequently large temperature differentials between night and day, on the order of 30° F. or more, which can cause an accumulation of moisture in the feed adjacent the cold metal of feed tanks or bins.

One reason why molds present such a serious problem is that they produce dangerous mycotoxins, some of which are carcinogenic. For example, one of the common molds, *Aspergillus flavus,* produces the mycotoxin aflatoxin which, in addition to other toxic characteristics, interferes with the immune system's ability to produce gamma globulin, the protein that represents the immune system. The resulting breakdown of the immune system then renders animals that have ingested such mold vulnerable to a variety of diseases.

The standard product that has been used for many years for the control of molds is propionic acid

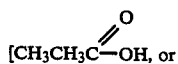

$[CH_3CH_3C\overset{O}{\underset{}{\parallel}}-OH$, or $CH_3CH_3COOH$ or $C_3H_7O_2]$. Prior to the present invention, propionic acid has been the most reliable mold inhibitor for animal feeds, and it still remains the product of choice on a worldwide basis. However, propionic acid has serious problems, so that it is unacceptable in many circumstances, and its use will be limited in some areas of the world, particularly in the Orient where the mold problem is most severe. A major problem with propionic acid is that it has a terrible, strong odor, which is almost like the smell of urine, and when people work around propionic acid their clothes and bodies acquire this obnoxious odor. One reason for this bad odor is that it is very volatile, so that it is rapidly released in vapor form from feeds to which it has been applied. For this reason, many people, and the people of some regions such as the Orient, will not stand for the use of propionic acid; and those who do use it are uncomfortable in such use. Also, some animals, particularly hogs, and also goats, are especially sensitive to the odor of propionic acid and will not touch feed that contains any useful amount of propionic acid in it.

The other principal problem with propionic acid is that it is highly corrosive. The only feasible place for propionic acid to be applied to feeds is in the feed plants or mills, and these are made of mild steel which is particularly vulnerable to acid corrosion. Thus, feed mills in which propionic acid is added to the feeds will rapidly deteriorate from the attack of this acid.

A number of mold inhibitor products combining propionic acid with other ingredients such as acetic acid and benzoic acid have been and are currently being marketed under a variety of trademarks in an endeavor to make the products more commercially acceptable, but the principal operative ingredient of such products is still propionic acid, and such products still have the same problems of the odor and corrosiveness of propionic acid.

It has been understood in the art that it is the propionate ion or radical $[CH_3CH_3COO$, or $C_3H_6O_2]$ that is the active mold inhibitor ingredient in propionic acid, so attempts have been made to use salts of propionic acid as mold inhibitors in an endeavor to overcome the odor and corrosion problems. The principal salts that have been used are the sodium and calcium salts of propionic acid, and as far as the applicant is aware, these have only been used as mold inhibitors in a fine, granular form, and never in the form of a liquid solution. These propionate salts do not have an objectionable odor, and are neutral and hence not especially corrosive. The sodium propionate salt has been found satisfactory in solid form for human use in bread, this being made possible because the granular or powdered sodium propionate disperses fairly well in the wet bread dough, remaining well dispersed throughout the baked bread.

Although currently used to a limited extent in animal feeds, the dry propionate salts are not satisfactory for feeds, the principal problem being that in granular form there is insufficient contact of the propionate salt particles with the grain particles unless great quantities of the propionate salts are used. On the order of five to seven times as much of the propionate salt must be used in order to disperse it adequately through the feed to get approximately the same degree of mold inhibition as can be achieved with liquid propionic acid. This makes the use of dry propionic salts such as sodium propionate and calcium propionate economically disadvantageous as mold inhibitors for animal feeds.

Prior to the present invention, propionic acid salts have never been usable in the form of a liquid solution for treating animal feeds, even though they would be equally as effective as mold inhibitors as propionic acid because it is the propionate ion which performs the mold inhibiting function, and the liquid would be readily dispersable in intimate contact with the feed grain particles in the same relatively small amounts as with liquid propionic acid, but without the objectionable odor and corrosive characteristics of the acid. It is believed that the principal reason why liquid propionic salt solutions have not heretofore been used as animal feed, mold inhibitors is the great propensity of the propionic salts to precipitate out of the solution in a mushy, gel-like form. This precipitation tendency is so great that a stable propionate salt solution of sufficient concentration to be a useful product has heretofore never been achieved. Even though adequate concentrations might have been achievable under controlled laboratory or plant conditions, the long-term stability was entirely inadequate for a useful mold inhibiting product.

There is also a serious mold problem which occurs in feeds that are stored in metal feed tanks or bins at locations where there are large overnight temperature drops, on the order of 30°-40° F., even with feeds that have a low moisture content. Such large temperature drops will lower the temperature of the feed bin or tank itself, establishing a large temperature differential between the walls of the tank or bin and the temperature of the feed within the central region of the tank. Water molecules have the characteristic of moving from a warmer zone toward a colder zone, and thus will move from the central region of the tank through the feed itself toward the cold walls of the tank, increasing the humidity and dampening the feed near the walls to provide an excellent growing medium for molds in that region; and this is recognized as a major problem when the humidity level increases to the point where moisture actually condenses on the walls of the tank. After a few repeated nights of a temperature differential on the order of 30°-40° F., mold spores which are present all of the time will become active and propagate. Even with feed having an average moisture content of 13.5 percent or less, which is normally considered to be safe from any substantial mold problem, the moisture content in the feed adjacent the tank walls will be raised higher and higher night after night of such temperature differentials, and a substantial mold problem will develop.

SUMMARY OF THE INVENTION

In view of these and other problems in the art, it is an object of the present invention to provide a liquid mold inhibitor usable for animal feedsthat is as effective as propionic acid, but does not have the objectionable odor and corrosion problems of propionic acid.

Another, general object of the present invention is to provide a liquid mold inhibitor which, because of its effectiveness and lack of objectionable characteristics, will be acceptable in all areas of the world, and most importantly in those tropical areas where propionic acid will not be used because of its bad odor and corrosive characteristics.

Another object of the invention is to provide a liquid mold inhibitor which comprises an aqueous solution of a salt of propionic acid, preferably sodium propionate, or alternatively potassium propionate or ammonium propionate, or any combination of these salts of propionic acid.

Another object of the invention is to provide a propionate salt solution mold inhibitor which includes one more deliquescent substances that serve the surprising function of preventing feed from becoming overly damp near the walls of feed bins that are subject to large overnight temperature differentials.

Another object of the invention is to provide a liquid propionate salt solution mold inhibitor of the character described which includes one or more humectants that trap odor-carrying moisture molecules in the liquid solution; the humecant also keeping the water content of the solution up so that the salt remains fully hydrolyzed and thereby fully functional as a mold inhibitor; and the humectant also cooperating with the deliquescent material in preventing water molecules from moving through feed bins and concentrating in the feed proximate cold feed bin walls.

A further object of the invention is to provide a liquid mold inhibitor comprising a propionate salt solution which has long-term stability against precipitation, yet which is sufficiently concentrated to be a useful product.

Yet a further object of the invention is to provide a method of making a propionate salt solution suitable for use as an animal feed mold inhibitor, yet which has no objectionable odor or corrosion characteristics.

The product of the invention is an aqueous solution of a salt of propionic acid, which may be sodium propionate, ammonium propionate, or potassium propionate, or any combination of these, but preferably is sodium propionate because that is the easiest of the three to work with and has no objectionable characteristics. The propionate salt solution is not nearly as volatile as propionic acid, which greatly reduces the odor. The propionate salt solution is also substantially neutral, instead of being highly acidic as is propionic acid, so that the solution is generally non-corrosive, having corrosive characteristics approximating those of water. The pH of the solution is preferably in the range of from approximately 6.3 to approximately 6.9, and is most preferably in the range of from approximately 6.5 to approximately 6.7. The solution also includes a humectant, which cooperates with the use of propionate salt instead of propionic acid in further controlling odor by inhibiting the moisture molecules from escaping from the liquid and thereby locking odor-carrying moisture in the solution, the humectant at the same time stabilizing the relative proportions of the other ingredients in the solution.

Where the feed is to be kept in a closed metal tank or bin rather than being left in the open, one would normally expect the presence of a deliquescent material to be harmful by pulling moisture out of the air and thereby increasing the moisture content of the feed and making it more vulnerable to the growth of mold. However, the applicant has found that, to the contrary, the addition of a deliquescent material has the surprising result of greatly reducing the propagation of mold in feed bins that are subject to large nighttime temperature drops by preventing moisture from moving toward the cold tank walls and accumulating in the feed adjacent the walls. The humectant cooperates with the deliquescent material in such stabilization of the location of the water molecules throughout the tank.

An additional ingredient that may be included in the solution, particularly where the solution is to be used on feed intended for hogs and also for goats, is monosodium glutamate (MSG).

DETAILED DESCRIPTION

The method of the present invention for producing the product of the invention is believed most clearly understandable by a description of the production of a specific batch weight of the product with the ingredients in relative proportions that will produce a presently preferred embodiment of the product. The total batch weight for the example given is 300 lbs., and the product to be produced is an aqueous solution of sodium propionate in which the humectant is glycerine, and which includes MSG. In this example, the MSG will be made during the process by including hydrochloric acid and glutamic acid among the ingredients.

For this 300 lb. batch, the ingredients and amounts thereof by weight are as follows:

26.5 lbs. water
3.3 lbs. "concentrated" hydrochloric acid [HCl]
3.6 lbs. 100% glutamic acid [$C_5H_8O_4N$, or COOHCH$_2$CHCHNH$_2$COOH—a dibasic acid]
7.25 lbs. 100% glycerine
3.0 lbs. deliquesscent material consisting of 1.5 lbs. magnesium chloride, 1.0 lbs. calcium chloride, 0.3 lb. manganese chloride, 0.1 lb. ferric chloride, and 0.1 lb. zinc chloride 110.0 lbs. 50% sodium hydroxide [NaOH]
146.35 lbs. 100% propionic acid

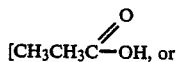

[CH$_3$CH$_3$C—OH, or

CH$_3$CH$_3$COOH, or C$_3$H$_7$O$_2$]

The hydrochloric acid and glutamic acid are added to the water before the water is added to another of the ingredients except possibly the glycerine, and this will produce glutamic acid monohydrochloride, as follows:

C$_5$H$_8$O$_4$N + HCl — C$_5$H$_8$O$_4$·HCl

This procedure is required in order to get the glutamic acid into solution; otherwise it would not dissolve.

The glycerine is added to the water, preferably after the hydrochloric acid and glutamic acid have been added; but if desired, the glycerine may be added to the water before the hydrochloric acid and glutamic acid.

The deliquescent material is added to the water, preferably after the hydrochloric acid glutamic acid have been added; but if desired, the deliquescent material may be added to the water before the hydrochloric acid and glutamic acid.

Then, preferably the next step is to dilute the propionic acid with the water which already contains the glutamic acid monohydrochloride and the glycerine and deliquescent material, and then the sodium hydroxide is added to the mixture. Alternatively, the sodium hydroxide may be diluted with the water which contains the glutamic acid monohydrochloride, and then the propionic acid added to this mixture. The first of these two alternatives is preferred, because when the water is added to the sodium hydroxide a large amount of heat is generated, and by having the large quantity of propionic acid already present when the sodium hydroxide is added, the propionic acid will serve as a heat sink and the thermal activity will be reduced.

The chemical reaction of the propionic acid with the sodium hydroxide is as follows:

Propionic Acid + Sodium Hydroxide ⟶

Sodium Propionate + Water or

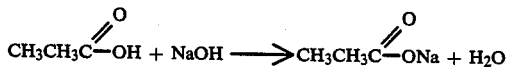

CH$_3$CH$_3$C—OH + NaOH ⟶ CH$_3$CH$_3$C—ONa + H$_2$O

Sodium propionate may alternatively be designated as follows:

C$_3$H$_6$O$_2$Na, or CH$_3$CH$_3$COONa

Addition of sodium hydroxide directly to propionic acid in an attempt to provide a sodium propionate solution produces such a serious precipitation problem as to preclude the formation of a sufficiently concentrated product with long-term stability to be useful as a mold inhibitor for animal feeds. However, according to the present process all of the other ingredients, including the water, glycerine, hydrochloric acid and glutamic acid, have already been placed in one of the solutions before the sodium hydroxide and propionic acid are brought together, and applicant has found that this has diluted out the number of molecules per unit of space sufficiently to produce a solution after completion of the reaction with all of the ingredients fully dissolved that is sufficiently concentrated and has a sufficient long-term stability for use as a mold inhibitor product for animal feeds.

During the reaction, the hydrochloric acid component of the glutamic acid monohydrochloride will be neutralized by the sodium hydroxide and thereby removed from the glutamic acid, and the glutamic acid will react with the sodium hydroxide to produce MSG, as follows:

Glutamic Acid + Sodium Hydroxide ⟶

Monosodium Glutamate + Water or

C$_5$H$_8$O$_4$ + NaOH ⟶ C$_5$H$_7$O$_4$Na + H$_2$O

For this 300 lb. batch example, there is 48.8 percent propionic acid by weight, of which 98.65 percent by weight is propionate ion. Thus, in the product of the invention that is produced there is 48.14 percent by weight of propionate ion.

If the MSG is to be added as MSG instead of being formed during the process by getting it into solution with hydrochloric acid and reacting it with sodium hydroxide, then the MSG is preferably added to the water before the water is combined with the other ingredients of the product. For the foregoing 300 lb. batch, the 3.6 lbs. of glutamic acid that was used in the formulation will result in 4.14 lbs. of MSG in the final product. Accordingly, if the MSG is not made during the process but is added at the end of the formulating procedure, 4.14 lbs. of MSG will be added to make the presently preferred 300 lb. batch formulation. In that case, without the presence of hydrochloric acid as one of the ingredients, in order to neutralize the product 3.7 lbs. less of sodium hydroxide will be used, and then to make up the same batch weight and relative amounts of the ingredients in the batch, water will be added in the amount of 3.7 lbs. Such water is preferably added prior to the mixing together of the sodium hydroxide and propionic acid in accordance with the procedure referred to above of diluting out the number of molecules per unit of space as much as possible to work against the precipitation problem.

In the final product, the sodium propionate ionizes in the solution to become:

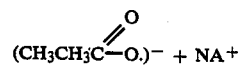

(CH$_3$CH$_3$C—O.)$^-$ + NA$^+$

It is this propionate ion which is the effective mold inhibitor in the product, and it inhibits mold in the same way and with the same efficacy as the corresponding propionate ion does in propionic acid, but without the offensive odor and corrosiveness of the propionic acid.

While the specific ingredients and proportions thereof given in the above 300 lb. batch example constitute a presently preferred product according to the invention, it is to be understood that the invention is not limited to such specific proportions, or to such specific ingredients as indicated below. The preferred range for the amount of propionate ion in the product is from approximately 20 percent to approximately 55 percent by weight equivalent of propionic acid (of which 98.65 percent by weight is propionate ion), while the most preferred range is from approximately 40 percent to approximately 55 percent weight equivalent of propionic acid.

The pH of the present mold inhibiting product is preferably in the range of from approximately 6.3 to approximately 6.9, and most preferably in the range of from approximately 6.5 to approximately 6.7, which, although slightly acidic, is a substantially neutral state, and in the 300 lb. batch example, the pH is approximately 6.6.

While sodium hydroxide is the preferred base to be employed in the formulation as it is easier to handle than ammonium hydroxide and more economical than potassium hydroxide, it is to be understood that ammonium hydroxide and potassium hydroxide will also work well, or any combination of these three hydroxides may also be employed.

While glycerol is the preferred humectant, other suitable humecants include potassium polymetaphosphate, propylene glycol, sorbitol, triacetin, mannitol, any of the pectins, and any of the polyhydric alcohols. Any combination of these humectants may also be used if desired. The preferred range for the amount of humectant in the product is from approximately 1.0 percent to approximately 4.0 percent by weight, and in the above 300 lb. batch example, there is approximately 2.42 percent by weight of glycerol.

The presently preferred range for the amount of deliquescent material in the product is from approximately 0.5 percent to approximately 10.0 percent, while the most preferred range is from approximately 1.0 percent to approximately 4.0 percent. In the above 300 lb. batch example, there is 1.0 percent by weight of the deliquescent material.

The presently preferred deliquescent material is one or more deliquescent substances from the group consisting of magnesium chloride, calcium chloride, manganese chloride, ferric chloride, and zinc chloride. Nevertheless, the deliquescent material may be any one or more deliquescent chemicals from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorous oxide, potassium acetate, potassium carbonate, potassium iodide, potassium phosphate, sodium bisulphate, stannic sulphate, and zinc chloride.

The presently preferred range for MSG is from approximately 1.15 percent to approximately 3.45 percent by weight (from approximately 1 percent to approximately 3 percent by weight for the glutamic acid if the MSG is made in the process). In the above 300 lb. batch example, the MSG constitutes approximately 1.47 percent by weight. However, where the product is not to be used in hog (or goat) feed, then the MSG need not be included.

It is to be understood that in carrying out the method of the invention as described above, the ingredients are to be mixed as required at the various stages.

EXAMPLE 2

Applicant has prepared a 100 lb. batch of the product of the invention as follows:
The ingredients for this batch were:
10.8 lbs. water
1.3 lbs. 100% MSG
2.3 lbs. 100% glycerine
1.0 lb. deliquescent material, consisting of approximately 0.5 lb. magnesium chloride, 0.33 lb. calcium chloride, 0.1 lb. magnesium chloride, 0.003 lb. ferric chloride, and 0.033 lb. zinc chloride
36.4 lbs. 50% sodium hydroxide
48.2 lbs. 100% propionic acid First, the MSG was mixed and dissolved in the water. Then the glycerine and deliquescent material were added to the water and mixed. Then the sodium hydroxide was added to the water/MSG/sodium hydroxide and mixed. Finally, the propionic acid was added to the other ingredients and mixed. The reaction was then allowed to proceed to completion, resulting in a mold inhibiting product according to the invention having the following relative proportions by weight of the ingredients:
10.8% water
1.3% MSG
2.3% glycerine
1.0% deliquescent material
48.2% propionic acid (of which 98.65% is propionate ion)

The great reduction of odor appears to be achieved in the present invention by a synergistic cooperation between the substantial neutralization of propionic acid and the humectant. The substantially neutral propionic salt solution has a much lower volatility than propionic acid, which greatly reduces the evaporation of odor-carrying moisture, to a sufficiently low level for the humectant to be able to substantially completely "lock in" the odor. Without such reduction of volatility by the neutralization, the humectant would be ineffective. A humectant has heretofore been used by applicant for control of evaporation, but applicant is not aware of any prior use of a humectant coupled with neutralization for odor control, or of any such use for animal feed. In applicant's prior U.S. Pat. No. 4,008,332, issued Feb. 15, 1977 for "Microcide," a humectant and a deliquescent were used to prevent evaporation of a very thin film of Microcide-containing moisture on a relatively short-term basis.

The water that is added into the product serves three distinct purposes. First, it serves to dilute out the number of molecules per unit of space as much as possible during manufacture of the product prior to the encounter between the propionic acid and the base, thereby minimizing the severe precipitation problem that normally would occur when these two ingredients are mixed. Second, the water enables the salt of propionic acid contained in the product to be substantially uniformly dispersed when the product is applied to the feed. Third, the water hydrolyzes the salt of propionic acid and thereby enables the salt to most efficiently perform its function as a mold inhibitor. While the primary function of the humectant is to "lock in" the odor, it also keeps the water that was added during the manufacture of the present product from evaporating, thereby maintaining the salt of propionic acid hydrolyzed and fully functional over a long operational life of the product.

The deliquescent material serves a completely new and unexpected function in this art where feeds are kept in metal tanks or bins, which is a widespread practice. This function is the opposite of what those skilled in the art would expect the function of a deliquescent material to be. It would be expected that the deliquescent material would draw in moisture from the air trapped in the feed bin each time the cover of the bin were opened and then reclosed, and thereby raise the moisture level within the feed and in due course increase the moisture to a level at which the feed is vulnerable to the propagation of mold.

The new function of the deliquescent material in the combination with the mold retardant salt of propionic acid is based upon the problem in feed bins that where the bins are located in climates where there is a large nighttime temperature drop, on the order of 30°–40° F., which is the case in many climates particularly during the spring and fall seasons. The large overnight drop in temperature of the metal of the feed bin causes large numbers of molecules to move from the generally warm interior of the mass of feed within the bin toward the cold metal walls of the bin, thereby increasing the dampness of the feed adjacent the walls of the bin. To illustrate this characteristic of water molecules moving from a warmer region toward a cold surface, attention is directed to the fact that considerable amounts of water will almost always condense on the exterior of a glass containing an iced drink, even though the air in that region may seem to be relatively dry.

It is generally recognized in the art that if the moisture content of feed can be kept down to a level of 13.5 percent or less by weight, then there will be no substantial mold problem. However, even if the average moisture content of the feed in a bin is only 13.5 percent, after a few successive nights during which the overnight temperature drop is on the order of 30°–40° F., movement of the water molecules through the feed from the central area toward the walls of the bin will raise the moisture content of the feed near the walls to a much higher percentage than the original 13.5 percent or less, creating a substantial mold problem in the peripheral regions of the bin. When the moisture movement to the walls of the bin reaches the stage where moisture is visibly condensing on the walls, then it is recognizable as a major mold problem.

There is a surprisingly large quantity of water available in feed for such movement of water molecules toward the walls of feed bins, even with a moisture content of the feed down to the 13.5 percent level generally considered safe against mold. Thus, at 13.5 percent moisture content, a 52 1 lb. bushel of feed contains 7.06 lbs. of water, which is approximely 3.5 quarts. If the 52 lb. bushel contained 16 percent moisture, which is typical for corn that is shipped, then this amounts to 8.32 lbs. of water, or approximately 1 gallon. To appreciate the tremendous number of water molecules involved in the problem of movement thereof toward the walls of feed bins, 7.06 lbs. of water, the amount in 1 bushel of feed at 13.5 percent moisture content, according to Avogadro's number (one molecular weight of any substance contains 6 times $10^{23}$ molecules) the 7.06 lbs. of water would contain 1.06 times $10^{26}$ water molecules, or 106 trillion trillion molecules of water. It will thus be seen that a very large amount of molecular traffic of water molecules can be caused to occur through a feed bin in response to a large overnight temperature drop.

This water molecule movement through the feed toward the walls of the bin has, surprisingly, been overcome by the presence of the deliquescent material in the product of the invention. The product, including the deliquescent material, is substantially uniformly distributed throughout the body of feed in the bin, and the deliquescent material has a greater affinity for all of the water molecules throughout the feed than the temperature differential attraction of the cold surfaces of the walls of the bin, so that the water molecules are substantially completely restrained from the usual movement toward the cold walls of the bin for all temperature fluctuations that would normally be expected. As a result, there is no observable increase in the moisture content of the feed adjacent the walls of the bin as compared with the moisture content of the feed throughout the remainder of the bin, and consequently there is no increased mold problem adjacent the walls of the bin. The humectant that is in the product of the invention and hence is also substantially uniformly dispersed throughout the feed cooperates with the deliquescent material in holding the water molecules against movement toward cold walls of the bin because of the attraction the humectant has for OH groups.

The liquid product of the invention is preferably applied to the feed at the feed mill, and will normally be applied in the mixer when the feed is being mixed. Such application can conveniently be made by use of a metering pump, the input end of which is placed in a drum of the mold inhibiting product, and the output end leading through a manifold which sprays the liquid mold inhibitor on the feed. Where a feed grain such as corn is rolled with the addition of steam, there is a particularly serious mold problem, which can best be controlled by applying the mold inhibitor of the invention right after the grain comes from the rollers. In feeds which contain molasses, a convenient way of applying the mold inhibitor liquid of the present invention is to mix it into the molasses before the molasses is added to the grain.

Experiments have shown that it is preferred to employ at least approximately 2 lbs. of the liquid mold inhibitor of the invention per ton of feed to assure long-term protection against mold in most environments. For severe mold problems, considerably more of the product may be desirable. For example, in the most severe grain mold problem of which applicant is aware, the brewers wet grains problem, it may be desirable to use up to approximately 10 lbs. of the product per ton of the wet grains. In an experiment with brewers wet grains, which normally start to mold within about 24 hours, applicant employed 10 lbs. per ton of the present product and after 3 weeks of observation there was no mold whatsoever observable.

In summary, the method of the present invention has, for the first time, produced a completely satisfactory mold inhibiting product for use with animal feed grains, the product having no objectionable odor or corrosion characteristics, so that the product is comfortable to use and should be acceptable on a worldwide basis. This product has been found experimentally to be fully acceptable by even the most sensitive animals such as hogs, and will not contaminate workers with an objectionable odor.

While presently preferred ranges have been set forth herein for the proportions of the ingredients of the product of the invention, and for the amount of product to be used in feeds, it is to be understood that such ranges have not been given by way of limitation, and that other proportions may be usefully employed within the scope of the invention.

It is also to be understood that although the present invention has been described for use in curing the animal feed mold problem, it is fully applicable to a variety of other mold problems. Accordingly, the invention is not intended to be limited to use in connection with animal feeds.

While the present invention has been described herein in what is conceived to be the most practical and preferred embodiment, it is recognized that departures may be made therefrom within the scope of the invention, which is therefore not to be limited to the details disclosed herein, but is to be accorded the full scope of the claims.

I claim:

1. A mold inhibitor composition which comprises, in aqueous solution:
   at least one salt of propionic acid from the group consisting of sodium propionate, potassium propionate and ammonium propionate;
   at least one deliquescent substance from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phophorus oxide, potassium acetate, potassium carbonate, potassium iodide, potassium phosphate, sodium bisulphate, stannic sulphate, and zinc chloride; and
   at least one humectant from the group consisting of glycerol, potassium polymetaphosphate, propylene glycol, sorbitol, triacetin, and mannitol.

2. A mold inhibitor composition as defined in claim 1, wherein said at least one deliquescent substance is from the group consisting of magnesium chloride, calcium chloride, manganese chloride, ferric chloride and zinc chloride.

3. A mold inhibitor composition as defined in claim 2, wherein:
   the amount of propionate ion in said composition is in the range of from approximately 20 percent to approximately 55 percent by weight equivalent of propionic acid; and
   the amount of said deliquescent substance(s) is in the range of from approximately 0.5 percent to approximately 10 percent by weight.

4. A mold inhibitor composition as defined in claim 2, wherein:
   the amount of propionate ion in said composition is in the range of from approximately 40 percent to approximately 55 percent by weight equivalent of propionic acid; and
   the amount of said deliquescent substance(s) is in the range of from approximately 1 percent to approximately 4 percent by weight.

5. A mold inhibitor composition as defined in claim 1, wherein:
   the amount of propionate ion in said composition is in the range of from approximately 20 percent to approximately 55 percent by weight equivalent of propionic acid; and
   the amount of said deliquescent substance(s) is in the range of from approximately 0.5 percent to 10 percent by weight.

6. A mold inhibitor composition as defined in claim 5, wherein said salt of propionic acid comprises sodium propionate.

7. A mold inhibitor composition as defined in claim 1, wherein:
   the amount of propionate ion in said composition is in the range of from approximately 40 percent to approximately 55 percent by weight equivalent of propionic acid; and
   the amount of said deliquescent substance(s) is in the range of from appoximately 1 percent to approximately 4 percent by weight.

8. A mold inhibitor composition which comprises, in aqueous solution:
   at least one salt of propionic acid from the group consisting of sodium propionate, postassium propionate and ammonium propionate; and
   all five deliquescent substances from the group consisting of magnesium chloride, calcium chloride, manganese chloride, ferric chloride and zinc chloride.

9. A mold inhibitor composition which comprises, in aqueous solution:
   at least one salt of propionic acid from the group consisting of sodium propionate, potassium propionate and ammonium propionate;
   at least one deliquescent substance from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium choloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride; and
   at least one humectant from the group consisting of glycerol, potassium polymetaphosphate, propylene glycol, sorbitol, triacetin, and mannitol;
   the amount of propionate ion in said composition being in the range of from approximately 20 percent to approximately 55 percent by weight equivalent of propionic acid;
   the amount of said deliquescent substance(s) being in the range of from approximately 0.5 percent to 10 percent by weight; and
   the amount of said humectant(s) being in the range of from approximately 1 percent to approximately 4 percent by weight.

10. A mold inhibitor composition as defined in claim 9, wherein said humectant comprises glycerol.

11. A mold inhibitor composition as defined in claim 9, where said salt of propionic acid comprises sodium propionate and said humectant comprises glycerol.

12. A mold inhibitor composition as defined in claim 11, wherein said at least one deliquescent substance is from the group consisting of magnesium chloride, calcium chloride, manganese chloride, ferric chloride and zinc chloride.

13. A mold inhibitor composition as defined in claim 9 which has a pH in the range of from approximately 6.3 to approximately 6.9.

14. A mold inhibitor composition which comprises, in aqueous solution:
- at least one salt of propionic acid from the group consisting of sodium propionate, potassium propionate and ammonium propionate;
- at least one deliquescent substance from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lacttate, ferric nitrate, ferrous iodide, magnexium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride; and
- at least one humectant from the group consisting of glycerol, potassium polymetaphosphate, propylene glycol, sorbitol, triacetin, and mannitol;
- the amount of propionate ion in said composition being in the range of from approximately 40 percent to approximately 55 percent by weight equivalent of propionic acid; and
- the amount of said humectant(s) being in the range of from approximately 10 percent to approximately 4 percent by weight.

15. A mold inhibitor composition which comprises, in aqueous solution:
- at least one salt of propionic acid from the group consisting of sodium propionate, potassium propionate and ammonium propionate;
- at least one deliquescent substance from the group consisting of magnesium cloride, calcium chloride, manganese chloride, ferric chloride and zinc chloride; and
- at least one humectant from the group consisting of glycerol, potassium polymetaphosphate, propylene glycol, sorbitol, triacetin, and mannitol;
- the amount of propionate ion in said composition being in the range of from approximately 20 percent to approximately 55 percent by weight equivalent of propionic acid;
- the amount of said deliquescent substance(s) being in the range of from approximately 0.5 percent to approximately 10 percent by weight; and
- the amount of said humectant(s) being in the range of from approximately 1 percent to approximately 4 percent by weight.

16. A mold inhibitor composition which comprises, in aqueous solution:
- at least one salt of propionic acid from the group consisting of sodium propionate, potassium propionate and ammonium propionate;
- at least one deliquescent substance from the group consisting of magnesium chloride, calcium chloride, manganese chloride, ferric chloride and zinc chloride; and
- at least one humectant from the group consisting of glycerol, potassium polymetaphosphate, propylene glycol, sorbitol, triacetin, and mannitol;
- the amount of propionate ion in said composition being in the range of from approximately 40 percent to approximately 55 percent by weight equivalent of propionic acid;
- the amount of said deliquescent substance(s) being in the range of from approximately 10 percent to approximately 4 percent by weight; and
- the amount of said humectant(s) being in the range of from approximately 1 percent to approximately 4 percent by weight.

17. A mold inhibitor composition which comprises, in aqueous solution:
- at least one salt of propionic acid from the group consisting of sodium propionate, potassium propionate and ammoniupropionate; and
- at least one deliquescent substance from the group consisting of of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride;
- the amount of propionate ion in said composition being in the range of from approximately 20 percent to approximately 55 percent by weight equivalent of propionic acid;
- the amount of said deliquescent substance(s) being in the range of from approximately 0.5 percent to 10 percent by weight; and
- said composition having a pH in the range of from approximately 6.3 to appoximately 6.9.

18. A mold inhibitor composition which comprises, in aqueous solution:
- at least one salt of propionic acid from the group consisting of sodium propionate, potassium propionate, and ammonium propionate;
- at least one deliquescent substance from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorous oxide, potassium acetate, sodium bisulphate stannic sulphate, and zinc chloride; and
- said composition further comprising monosodium glutamate.

19. A mold inhibitor composition as defined in claim 18, wherein:
- the amount of propionate ion in said composition is in the range of from approximately 20 percent to approximately 55 percent by weight equivalent of propionic acid;
- the amount of said deliquescent substance(s) is in the range of from approximately 0.5 percent to 10 percent by weight; and wherein said monosodium glutamate is in an amount in the range of from approximately 1.15 percent to approximately 3.45 percent by weight.

20. A mold inibitor composition as defined in claim 18, wherein:
said composition further comprises at least one humectant from the group consisting of glycerol, potassium polymetaphosphate, propylene glycol, sorbitol, triacetin, and mannitol;
the amount of said humectant(s) being in the range of from approximately 1 percent to approximately 4 percent by weight; and
wherein said monosodium glutamate is in an amount in the range of from approximately 1.15 percent to approximately 3.45 percent by weight.

* * * * *